United States Patent
Uzgiris et al.

(10) Patent No.: US 7,901,665 B2
(45) Date of Patent: Mar. 8, 2011

(54) CONJUGATED MACROMOLECULES

(75) Inventors: Egidijus Edward Uzgiris, Schenectady, NY (US); Brian James Grimmond, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1496 days.

(21) Appl. No.: 11/290,684

(22) Filed: Nov. 30, 2005

(65) Prior Publication Data

US 2007/0122346 A1    May 31, 2007

(51) Int. Cl.
*A61K 50/00* (2006.01)
*A61M 36/14* (2006.01)

(52) U.S. Cl. .................................... 424/1.11; 424/1.65

(58) Field of Classification Search .................. None
See application file for complete search history.

(56) References Cited

U.S. PATENT DOCUMENTS

| 5,681,544 A | 10/1997 | Schmitt-Willich et al. |
| 6,274,713 B1 | 8/2001 | Sieving et al. |

OTHER PUBLICATIONS

Uzgiris et al. (Biomacromolecules 2004, 5, 54-61).*
Buckley et al. (FEBS, 1984, 166, 202-204).*
Urizzi et al. (Tett. Lett. 1996, 37, 4685-4688).*
Slinkin et al., "Terminal-Modified Polylysine-Based Chelating Polymers: Highly Efficient Coupling to Antibody with Minimal Loss in Immunoreactivity," *Bioconjugate Chem.* 1981, 2, pp. 342-348.
Huber et al., "Fluorescently Detectable Magnetic Resonance Imaging Agents," *Bioconjugate Chem.* 1998, 9, pp. 242-249.
Sieving et al., "Preparation and Characterization of Paramagnetic Polychelates and their Protein Conjugates," *Bioconjugate Chem.* 1990, 7, pp. 65-71.
Lewis et al., "A Facile, Water-Soluble Method for Modification of Proteins with DOTA. Use of Elevated Temperature and Optimized pH to Achieve High Specific Activity and High Chelate Stability in Radiolabeled Immunoconjugates," *Bioconjugate Chem.* 1994, 5, pp. 565-576.
Tsai et al., "Metabolism and Renal Clearance of 111ln-Labeled DOTA-Conjugated Antibody Fragments," *Bioconjugate Chem.* 2001, 12, p. 264.
Lewis et al., "An Improved Method for Conjugating Monoclonal Antibodies with N-Hydroxysulfosuccinimidyl DOTA," *Bioconjugate Chem.* 2001, 12, pp. 320-324.

* cited by examiner

*Primary Examiner* — Michael G Hartley
*Assistant Examiner* — Melissa Perreira
(74) *Attorney, Agent, or Firm* — Paul J. DiConza

(57) ABSTRACT

A method of conjugating a carboxylate-containing molecule to an amine-containing macromolecule to form a substituted macromolecule is provided. The method includes (a) forming a first solution by dissolving a substance comprising at least one macromolecule having free amine groups in an aqueous basic solution; (b) forming a second solution by combining at least one carboxylate-containing molecule with at least one acid acceptor in an aprotic solvent; (c) adding at least one carboxylate activating agent to the second solution to form an activated carboxylate-containing molecule; (d) combining the first solution and second solutions to form a multiphasic solution; and (e) isolating the resultant substituted macromolecule from the mixture. A substituted macromolecule produced by the aforementioned method is also provided. Further provided is a method of enhancing a magnetic resonance image of a subject including administering the carboxylate-containing molecule-substituted macromolecule produced by the aforementioned method.

36 Claims, 3 Drawing Sheets

Q = H, NEt₃ or other acid acceptor

CONJUGATED MACROMOLECULES

FIELD OF THE INVENTION

The present disclosure relates to methods for making conjugated macromolecules, the conjugated macromolecules made by the inventive methods, and uses for such conjugated macromolecules.

BACKGROUND

The pharmacokinetics (e.g., the biodistribution and the plasma half-life) of agents that are introduced into a subject may be critical to the utility of agents that are used to diagnose or treat a subject. The signal intensity of an imaging agent may be improved by clustering multiple units of the agent into a platform construct, for example a macromolecule. The pharmacokinetics and signal intensity of small molecule agents may be improved by attaching the small molecule to a macromolecular that may be linear, branched, or cyclic synthetic polymers, polypeptides, proteins, antibodies, or carbohydrates. Such macromolecules may assume various structural conformations, for example, dendrimers, or nanoparticles.

Needs exist for methods of conjugating carboxylate-containing molecules to amine-containing macromolecules that consistently provides high yields of substantially pure macromolecular conjugates and reduces the need for post-reaction purification steps.

SUMMARY

Provided herein are methods for conjugating macromolecules, conjugated macromolecules prepared by the disclosed methods, and uses for the conjugated macromolecules.

In general, the disclosed methods include the steps of: (a) forming a first solution by dissolving a substance comprising at least one macromolecule having free amine groups in an aqueous basic solution; (b) forming a second solution by combining at least one carboxylate-containing molecule with at least one acid acceptor in an aprotic solvent; (c) adding at least one carboxylate activating agent to the second solution to form an activated carboxylate-containing molecule; (d) combining the first solution and second solutions to form a multiphasic solution; and (e) isolating the resultant substituted macromolecule from the mixture. Step (c) should follow step (b), otherwise the order of the steps (a)-(c) may be alternated. Thus, for example, in some embodiments step (a) may follow step (c). Similarly, the first solution may be added to the second solution or vice versa.

In some embodiments, the second solution is maintained at a temperature below about −40° C. In other embodiments, the first solution is an aqueous basic solution with an initial pH in the range of between about 9 and about 12. In still other embodiments, the first solution has a pH of about 10.

Both the first solution and the second solution may be miscible under ambient reaction conditions. The first solution may comprises an additive that separates the first solution and second solution into more than one phase. In some embodiments, the additive causes the phase separation by increasing ionic strength of the first solution. The additive may comprise at least one salt. Such a salt may be alkali and alkaline earth metal halides, or combinations thereof. Exemplary salts may include: NaCl; LiCl, KBr, KF, $MgCl_2$, $CaCl_2$, which may be used in combination In some embodiments, the at least one carboxylate-containing molecule includes a metal chelator, for example, DTPA, EDTA, DOTA, p-SCN-Bz-DOTA, DO3A, DOTMA, B-19036, NOTA, TETA, TTHA, CYDTA, HP-DO3A, CDTA, CDTPA, OTTA, or combinations thereof. The carboxylate-containing molecule may further comprise one or more radioactive ion. Such radioactive ion may include: actinium-225, bismuth-212, arsenic-72, indium-110, indium-111, indium-113m, gallium-67, gallium-68, strontium-83, zirconium-89, ruthenium-95, ruthenium-97, ruthenium-103, ruthenium-105, mercury-107, mercury-203, rhenium-186, rhenium-188, tellurium-121m, tellurium-122m, tellurium-125m, thulium-165, thulium-167, thulium-168, technetium-94m, technetium-99m, silver-111, platinum-197, palladium-109, copper-62, copper-64, copper-67, yttrium-86, yttrium-90, scandium-47, samarium-153, lutetium-177, rhodium-105, praseodymium-142, praseodymium-143, terbium-161, holmium-166, gold-199, cobalt-57, cobalt-58, chromium-51, iron-59, selenium-75, thallium-201, ytterbium-169; or combinations thereof.

The carboxylate-activating agent may be selected from alkylchloroformates, EDC, DCC, CDI, EDC/NHS, DCC/NHS, EDC/NHSOSu, DCC/NHSOSu, phenolic coactivators, or combinations thereof. In some embodiments, the carboxylate-activating agent comprises isobutylchloroformate.

Acid acceptors useful in step (b) may include triethylamine, trimethylamine, N,N,N',N'-tetramethylethylenediamine, N,N,N',N'-tetramethyl-1,8-napthalenediamine, N-methylmorpholine, pyridine, N,N-dimethylaminopyridine, 1,5-diazobicyclo[4.3.0]non-5-ene, 1,5-diazobicyclo[5.4.0]undec-5-ene, 1,4-diazobicylo[2.2.2]octane, 1,1,3,3-tetramethylguanidiune, or combinations thereof. In some preferred embodiments, the acid acceptor comprises triethylamine. Furthermore, the aprotic solvent used in step (b) may be selected from acetonitrile, methylene chloride, chloroform, ethylene dichloride, tetrahydrofuran, 1-methyl-2-pyrrolidinone, dimethylformamide, dimethyl sulfoxide, or combinations thereof. In some embodiments, the aprotic solvent comprises acetonitrile.

In some embodiments, the optionally-glycosylated macromolecule may be selected from polymeric amino acids, amino sugars, hormones, hormone-like molecules, antibiotics, aminated carbohydrates, cofactors, aminated dendrimers, aminated nanoparticles, or combinations thereof. Additionally, the macromolecule may comprise a poly(lysine) salt (e.g., poly(lysine hydrobromide)) or a protein (e.g., immunoglobulins, antibodies, or human serum albumin).

In embodiments where the macromolecule comprises amine-bearing multiple repeat units, at least two equivalents of carboxylate containing molecule may be used per one equivalent of the macromolecule repeat unit in steps (a) and (b). In alternative embodiments, at least four equivalents of carboxylate containing molecule are used per one equivalent of the macromolecule repeat unit.

In yet other embodiments, the macromolecule comprises multiple repeat units and at least 95 percent of the macromolecule repeat units are conjugated with the carboxylate-containing molecule. Using the methods disclosed herein, may yield at least 60%, at least about 90%, at least about 95%, or at least about 99% of the substituted macromolecule.

In some embodiments, the at least one carboxylate-containing molecule comprises DTPA, the at least one acid acceptor comprises triethylamine, the aprotic solvent comprises acetonitrile, the at least one alkyl chloroformate comprises isobutylchloroformate, and the macromolecule comprises poly(lysine) salt. In other embodiments, the aqueous sodium bicarbonate solution has a pH in the range of between about 9 and about 10, the DTPA-substituted polymer is at least 96 percent conjugated, and the yield of the Gd DTPA substituted polymer is at least about 67%.

The residence time of the activated carboxylate-containing molecule in the second solution may be less than 10 minutes during addition to the first solution. Alternatively, the residence time of the activated carboxylate-containing molecule in the second solution is less than about 5 minutes during addition to the first solution.

In another aspect, the present disclosure provides methods of enhancing a magnetic resonance image of a subject (e.g., a human) comprising administering a carboxylate-containing substituted macromolecule produced by the disclosed methods labeled with a paramagnetic or superparamagnetic chemical in a pharmaceutically acceptable carrier to the subject.

DESCRIPTION OF THE FIGURES

While the novel features of the invention are set forth with particularity in the appended claims, the invention, both as to organization and content, will be better understood and appreciated, along with other objects and features thereof, from the following detailed description taken in conjunction with the following figures.

DETAILED DESCRIPTION

Figure 1:
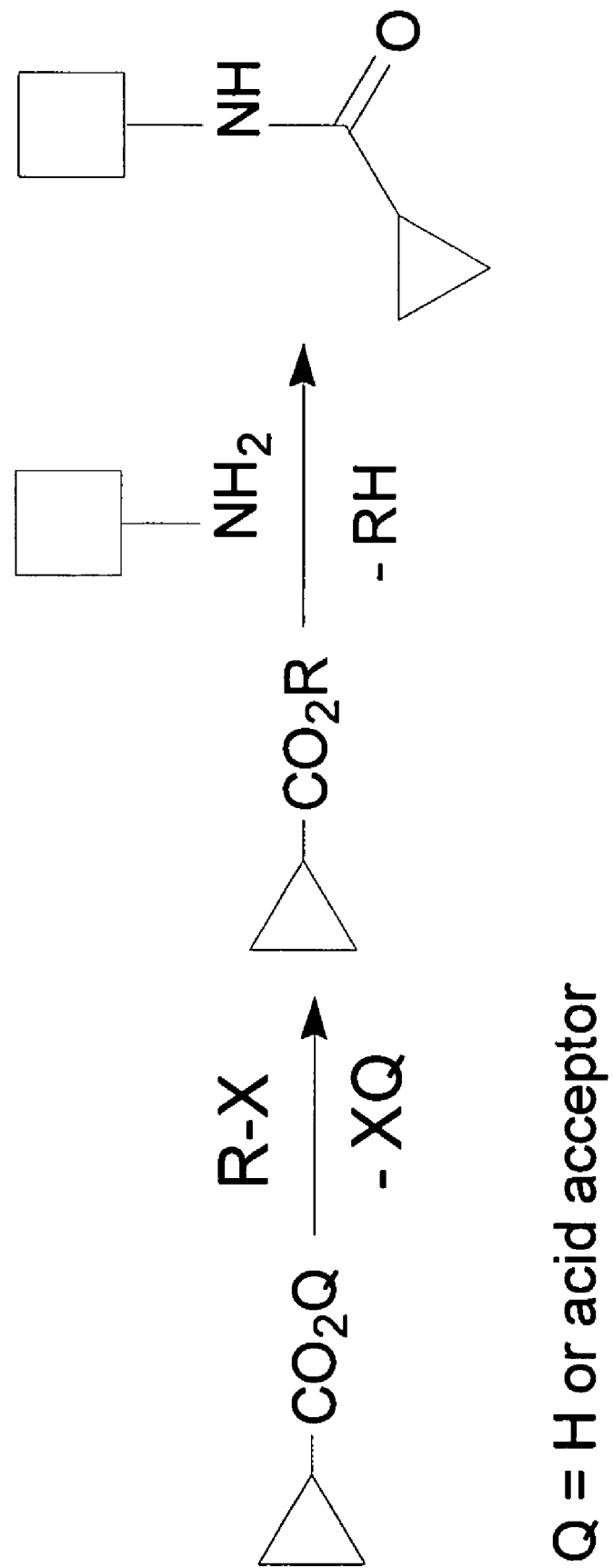
FIG. 1 depicts the activation of a carboxylate-containing molecule to provide an activated carboxylate-containing molecule that is then conjugated to an amine-containing macromolecule to form a substituted macromolecule.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Each numerical parameter should at least be construed in light of the number of reported significant digits and by applying ordinary rounding techniques.

To more clearly and concisely describe and point out the subject matter of the claimed invention, the following definitions are provided for specific terms, which are used in the following description and the appended claims.

As used herein, the term "acid acceptor" generally refers to basic compounds that may be used to quench an acid functional group. The acid acceptors used in the disclosed methods may also increase the aprotic solvent solubility of the carboxylate-containing molecule in the present invention. Illustrative acid acceptors may include triethylamine, trimethylamine, N,N,N',N'-tetramethylethylenediamine, N,N,N',N'-tetramethyl-1,8-napthalenediamine, N-methylmorpholine, pyridine, N,N-dimethylaminopyridine, 1,5-diazobicyclo[4.3.0]non-5-ene, 1,5-diazobicyclo[5.4.0]undec-5-ene, 1,4-diazobicylo[2.2.2]octane, 1,1,3,3-tetramethylguanidiune, or combinations thereof.

As used herein, the terms "activating agent" and "activator" general refer to an agent or agents added to the mixture that cause a physical or chemical change to occur more rapidly or more completely than would occur without the activating agent. More specifically, activating agents useful in the disclosed methods activate carboxyl groups present in the carboxylate-containing molecules by chemically converting them to reactive intermediates such as active esters, anhydrides, carbonic anhydrides and so on, that react with amines to afford amides.

As used herein, the term "activated carboxylate-containing molecule" refers to the product that results from the combination of a carboxylate-containing molecule with an activating agent. In some embodiments, the activated carboxylate-containing molecule may comprise the active ester, anhydride, carbonic anhydride that may be formed from the combination of the carboxylate containing molecule and 1-ethyl-3-(3-dimethylaminopropyl)carbodiimide hydrohalide (EDC), dicyclohexylcarbodiimide (DCC), 1-cyclohexyl-3-(2-morpholino-ethyl) carbodiimide (CMC), carbonyldiimidazole (CDI), 1-ethyl-3-(3-dimethylaminopropyl) carbodiimide hydrohalide/N-hydroxysuccinimide (EDC/NHS), DCC/NHS, 1-ethyl-3-(3-dimethylaminopropyl) carbodiimide hydrohalide/N-hydroxy-sulfo-succinimide (EDC/NHSOSu), DCC/NHSOSu, or 1-ethyl-3-(3-dimethylaminopropyl)carbodiimide hydrohalide/nitrophenol.

As used herein, the term "aprotic solvent" refers to a solvent that does not yield or accept a proton. Aprotic solvents may include, but are not limited to acetonitrile; methylene chloride; chloroform; ethylene dichloride; tetrahydrofuran (THF); 1-methyl-2-pyrrolidinone (NMP); dimethylformamide (DMF); dimethyl sulfoxide (DMSO); and derivatives of any of the foregoing. In some embodiments, the aprotic solvent is acetonitrile, which may optionally be dry, nitrogen-purged acetonitrile.

As used herein the term "amine-containing molecule" refers to one or more of the repeat units or monomers containing an amine functional group (i.e., an amine group that is chemically accessible to modification). In some embodiments, the repeat unit naturally contains an amine functional group. In other embodiments, the molecule or monomer may be chemically modified to create the functional amine group. Illustrative amine-containing molecules include poly(lysine), poly(lysine)-(glutamic acid), poly(ornithine), poly(allylamine), poly(ethyleneimine), poly(amidoamine) dendrimers, bovine serum albumin, and/or human serum albumin.

As used herein, the term "carboxylate-containing molecule" refers to molecules containing a functional carboxylate group that may be appended to the amine-containing molecules. In some embodiments, the repeat unit naturally contains a carboxyl functional group. In other embodiments, the molecule or monomer may be chemically modified to create a functional carboxyl group. Carboxylate-containing molecules may include chelators, naturally occurring small molecules, and synthetic small molecules, natural and synthetic biomolecules. Thus, the phrase "carboxylate-containing molecules" is intended to embrace iodinated small molecules, fluorescent dyes (e.g., cyanine dyes), sugars (e.g., glucose), vitamins (e.g., folic acid), or combinations thereof (e.g., glycoproteins). The carboxylate-containing molecules may take any form, such as a nanoparticle or a dendrimer. Illustrative carboxylate-containing molecules may include doxorubicin, aspirin, sialic acid, iohexol, iodixanol, DTPA, DOTA, NOTA, TETA, Cy5.5, fluorescein, citric acid, folic acid, and/or biotin.

As used herein, the term "imaging moiety" generally refers to the functional portion of contrast agents that are useful for imaging a biological structure such as a specific organ or specific tissues. Image moieties includes moieties that generate images (e.g., radioactive isotopes) as well as those moieties that enhance (positively or negatively) images (e.g., paramagnetic ions and superparamagnetic ions). The image-enhancing moieties may be bound, covalently or non-covalently, to pendant groups (e.g., polydenate ligands, such as DTPA).

As used herein, the term "isolating" refers to the separation of the resultant substituted macromolecule from the reaction by-products using one or more standard isolation procedures. In some embodiments the isolation step may comprise extracting the substituted macromolecule from the reaction mixture. In alternative embodiments, the isolation step comprises removing the reaction by-product from the reaction mixture. Either approach may be accomplished using one or more standard separation technique including, for example, precipitation, chromatography, dialysis, and/or flow filtration methods (e.g., ultraflow filtration, and/or tangential flow filtration).

As used herein, the term "macromolecule" generally refers to chemical species comprising multiple repeat units that include amine-containing groups. In some embodiments, the macromolecules described herein have a molecular weight greater than about 2 KDa. In other embodiments, the macromolecules have a molecular weight greater than about 5 KDa. The macromolecule described herein may include a polyamino acid comprised of a single or multiple amino acids (e.g., lysine alone or lysine in combination with glutamic acid or aspartic acid). Furthermore, the macromolecules described herein may consist of both amino acid components and carbohydrate components, as is the case for glycoproteins. Any macromolecule having free amine groups may be used in the present invention to form the macromolecule/aqueous basic solution. The macromolecules described herein may comprise aminated molecules, such as amino acids, polymeric amino acids, polypeptides, proteins (e.g., enzymes, immunoglobulins, monoclonal antibodies and human serum albumin), enzymes, amino sugars and glycoproteins (e.g., lectins), hormones (e.g., insulin), hormone-like molecules (e.g., prostaglandins), antibiotics (e.g., bleomycins), aminated carbohydrates (e.g., aminated dextrans), cofactors (e.g., porphyrins), synthetic polymers and copolymers, aminated dendrimers, and aminated nanoparticles.

As used herein, the term "multiphasic solution" refers to more than one immiscible solution phase in a mixture. Thus, the solutions used in the disclosed conjugation methods may be biphasic, triphasic, etc. Where the phases are naturally miscible an agent, such as salt, may be added to mixture to induce phase separation. Typically, the phase-separation inducing agent is introduced at concentrations that induce phase separation but do not cause the macromolecule to precipitate out of solution. Thus, when the phase-separating inducing agent is a salt the solution is not supersaturated with the salt.

As used herein, the term "pendant group" refers to any functional group that may be appended to a macromolecule. Illustrative examples of pendant groups include, without limitation, ligands, chelators, fluorescent dyes, iodinated organic molecules, and polyethylene glycols. When the monomeric repeat unit of the macromolecule is lysine, the pendant group may be an amine-containing pendant group.

As used herein, the terms "percentage conjugation" and "degree of conjugation" refer to the level of conjugation of the pendant group per macromolecule. Using the disclosed conjugation methods one of ordinary skill in the art may control the percentage conjugation by varying the stoichiometric amount of the carboxylate-containing molecules. In one embodiment, a high percentage conjugation (e.g., greater than 90%) may be obtained by using four or more equivalents of the carboxylate-containing molecules for one equivalent of the amine-containing molecule.

As used herein the terms "pharmaceutically acceptable carrier" and "pharmaceutically acceptable carriers" refers to those compounds which are, within the scope of sound medical judgment, suitable for use in contact with the tissues of a subject without undue toxicity, irritation, allergic response, and the like, commensurate with a reasonable benefit/risk ratio, and effective for their intended use, as well as salts and biocompatible derivatives of those compounds.

As used herein the term "purity" refers to the presence of a single chemical entity or the absence of contaminants in a mixture. The purity of the conjugated molecule produced by the disclosed methods may be measured using standard analytical methods, for example, gel permeation chromatography (GPC) or high performance liquid chromatography (HPLC). When purity is measured by determining the amount of the resultant conjugated macromolecule measured using GPC, the purity may be greater than about 90%, greater than about 95%, or greater than about 99%. When the purity is measured by determining the amount of contamination GPC, contaminants such multimers of the conjugated molecule resulting from aggregation or cross linking may be less than about 20%, less than about 10%, or less than about 1%. Unless otherwise indicated, the values for purity described herein are measured following isolation by methods that do not substantially enrich the yield of a reaction.

As used herein the term "residence time" refers to the average length of time the carboxylate-containing molecule spends within the process vessel and/or process tubing. In some embodiments of the disclosed conjugation methods, the residence time that an activated carboxylate-containing molecule spends in solution at temperatures above the storage temperatures is minimized so as to reduce the decay of the activated agent. The residence time of the activated carboxylate-containing molecule may be reduced, for example, by forming the multiphasic mixture shortly after the formation of the activated carboxylate-activating agent. In some embodiments, the disclosed methods produce substituted macromolecules that are more than 90% pure, more than 95% pure, or more than 99% pure. The percentage conjugation may be reduced or increased by prolonging or shortening the residence time of the activated carboxylate-containing molecule, respectively. Thus, the combination of the residence time and stoichiometry of the carboxylate-containing molecule relative to the amine-containing molecule may be adjusted to control the percentage conjugation. Furthermore, vigorous mixing of the multiphasic mixture reduces aggregation and/or cross-linking thereby improving purity of the resultant macromolecule.

DESCRIPTION OF SPECIFIC EMBODIMENTS

Overview of Uses. The pharmacokinetics of agents that are introduced into a subject (e.g., non-human or human animal) to treat or image disease are critical to the efficacy of those agents. For example, image-enhancing moieties (e.g., paramagnetic or radioactive moieties) used in medical imaging may be toxic (e.g., heavy metals). One way to improve the pharmacokinetics of an agent (including reducing toxicity) involves binding or chelating the agent to a macromolecular platform (e.g., a naturally-occurring or synthetic macromolecule). The disclosed synthetic methods produce highly conjugated, highly pure, substituted macromolecules that are useful for, among other things, administration to a subject.

Therapeutic or imaging agents that may be synthesized using the disclosed methods may include agents comprising an imaging-enhancing moiety covalently bound to a macromolecule. The covalent bond may be direct through a functional group or indirect through a chemical linker attached to the functional group. Such agents may be synthesized by the activation of a carboxylate functional group within one reactant, by conversion to an active ester, anhydride or carbonic anhydride and the subsequent conjugation to an amine of the second reactant resulting in the formation of a covalent amide bond.

Polyaminocarboxylates are commonly used to chelate radionuclides and paramagnetic metals to produce macromolecules conjugated with pendant groups (e.g., ligands and chelators). Such pendant groups may be attached to amine-containing molecules by the activation of one carboxylate pendant group within the macromolecule upon binding to the pendant group. The resultant conjugated macromolecules are useful in various imaging modalities (e.g., PET, SPECT, or MRI).

General Scheme for Conjugating Macromolecules. Pendant groups may be covalently bound to a macromolecule, directly through a repeat unit functional group or indirectly by a chemical linker that is attached to the repeat unit functional group. The linkage may be accomplished by the activation of a carboxylate functional group within one reactant, by conversion to an active ester, anhydride or carbonic anhydride, and the subsequent conjugation to an amine of the second reactant resulting in the formation of a covalent amide bond. For example, polyaminocarboxylates are commonly used to chelate radionuclides and paramagnetic metals that are used in PET, SPECT, and MR imaging; these pendant groups can be attached to amine-containing macromolecular carriers by the activation of one carboxylate pendant group within the chelator and the diagnostic metal reporter then incorporates into the macromolecule upon binding to the chelator. However, the utility of this reaction is reduced because of the pH sensitive hydrolytic stability of the activated carboxylate intermediate that may be generated within an aqueous or buffered solution of the macromolecule. The resulting hydrolysis of the activated carboxylate containing moiety, prior to the coupling step, requires the use of multiple equivalents of reactant, often leads to difficulty in reproducing conjugation results, and is restricted to carboxylate containing reactants that are water soluble.

The expansion of the activation chemistry to include non-aqueous reactants and the reduction in the extent of the hydrolysis of the activated carboxylate-containing molecule may be accomplished by performing the carboxylate activation in a polar organic medium, such as acetonitrile, followed by combining the reagent with the macromolecule in an aqueous solution. However, the resulting combination of solvents often causes the irreversible precipitation or gelation of the hydrophilic macromolecular starting material. Removing such particulates introduces a lengthy purification procedure and low yield of the macromolecular conjugates.

Methods for Conjugating Macromolecules. When the activated carboxylate intermediate is moisture, pH, and/or thermally sensitive, some of the known processes for appending carboxylic pendant groups to amine containing macromolecules may result in precipitation of product due to aggregation, gelation or cross-linking of the polymer. Additionally, the hydrolysis of the activated carboxylate-containing moiety, prior to and during the coupling step, requires the use of multiple equivalents of reactant, and may lead to poor reproducibility and repeatability of the degree of conjugation and/or yield of the substituted macromolecule.

The disclosed alternate approach reduces the extent of activated carboxylate containing molecule hydrolysis and expands the applicability of the carboxylate activation to include non-aqueous conditions that minimize the irreversible aggregation, gelation and/or precipitation of the macromolecular starting material upon combination of the aqueous and non-aqueous reactant solutions.

Disclosed herein are methods for reproducibly conjugating pendant groups (e.g., carboxylate-containing molecules) onto numerous water-soluble polymers (e.g., macromolecules) with high yields. The disclosed methods reduce undesirable formation of cross-linked polymers and increase the purity of the resultant conjugated macromolecule.

Steps of the Disclosed Synthesis Methods. Methods of the invention may include dissolving a substance comprising at least one macromolecule having free amine groups (e.g., poly(lysine)) in an aqueous basic solution (e.g., sodium bicarbonate solution) to form a first solution. This first solution may have an initial pH in a range between about 9 to about 12. In some embodiments, the first solution has an initial pH of about 10. The first solution may, optionally, also comprise an additive that increases the ionic strength of the solution, such as a salt (e.g., NaCl LiCl, KBr, KF, $MgCl_2$ and $CaCl_2$). This optional additive is not required in cases to create a multiphasic solution when the two solutions are naturally miscible.

At least one carboxylate-containing molecule (e.g., DTPA) and at least one acid acceptor (e.g. triethylamine) in an aprotic solvent (e.g., acetonitrile) are then combined to form a second solution. The temperature of the second solution may be maintained below 0° C. during the addition of the at least one activating agent. In some embodiments, the temperature of the second solution is kept at or near −40° C.

At least one activating agent (e.g., IBCF) is then added to the second solution at or near −40° C. to generate the activated carboxylate-containing molecule (e.g., DTPA-isobutylcarbonic anhydride).

After the activated carboxylate-containing molecule has been generated, the second solution and the first solution are combined to form a mixture. In some embodiments, the first solution is added to the second solution. In alternative embodiments, the second solution is added to the first solution.

Whether the second solution is added to the first solution or vice versa, the residence time of the carboxylate-containing molecule is controlled. Thus, for example, when the second solution is added to the first solution, the carboxylate-containing molecule is quickly added to the second solution to minimize the residence time to thereby reduce decomposition of the activated carboxylate-containing molecule (e.g., activated DTPA such as DTPA-isobutylcarbonic anhydride). In some embodiments, residence time of the activated carboxylate-containing molecule is less than about 20 minutes, less than about 10 minutes, less than about 5 minutes, less than about 2 minutes, less than about 1.5 minute, or less than about 1 minute.

During or after the addition of the second solution to the first solution, the resulting mixture should be intermixed, for example by stirring or other mode of agitating a solution. In some embodiments, the intermixing results from vigorous stirring that is sustained for minutes, hours, or even days after the second solution has been added to the first solution. (See FIG. 1.)

Optional Isolation Step. The resulting substituted macromolecule may then be isolated from the mixture. In one embodiment, the mixture is transferred to a separatory funnel and allowed to settle into two or more phases. The aqueous phase is then separated and optionally added to an aqueous basic solution (with a pH at or near 10) comprising a salt to provide a clear colorless solution. The crude reaction mixture may then be purified by standard purification techniques, for example, tangential flow filtration (e.g., Pall Corporation suspended screen channel).

In one embodiment, the yield of the substituted macromolecule is at least about 60%, more preferably at least 65%, more preferably at least 70%, more preferably at least 75%, more preferably at least 80%, more preferably at least 85%, more preferably at least 90%. In another embodiment, a feature of a method of the invention provides a substituted macromolecule in yields ranging from about 60% to about 90%, and high purity. In various embodiments, the yield of the conjugated macromolecule is at least 70%, at least 75%, at least 80%, at least 85%, or at least 90%. In other embodiments, the conjugated macromolecule comprises at least 95%, at least 96%, at least 97%, at least 98%, or at least 99% of the final product.

Variations. Any macromolecule having free amine groups may be used in the present invention to form the substituted macromolecules. Thus, the disclosed conjugation methods may be used to conjugate pendant groups to aminated macromolecules comprised of polymeric amino acids (e.g., poly(lysine), poly(lysine-glutamic acid), poly(lysine-serine), and/or poly(ornithine)). The disclosed conjugation methods may further be used to conjugate pendant groups to macromolecules comprised of polypeptides in general as well as specific types of proteins (e.g., enzymes, immunoglobulins, monoclonal antibodies and human serum albumin), enzymes, amino sugars and glycoproteins (e.g., lectins), hormones (e.g., insulin), hormone-like molecules (e.g., prostaglandins), antibiotics (such as bleomycins), aminated carbohydrates (e.g., aminated dextrans), cofactors (e.g., porphyrins). Additionally, the pendant groups may be conjugated to macromolecules in various forms such as macromolecules configured as aminated dendrimers or aminated nanoparticles.

Any carboxylate-containing molecule may be used in the disclosed methods. Preferred carboxylate-containing molecules containing one or more acetic acid moiety. Illustrative examples of a carboxylate-containing molecule capable of reacting with an acid acceptors include, but are not limited to chelators such as diethylene triamine pentaacetic acid (DTPA); ethylene diamine tetraacetic acid (EDTA); 1,4,7,10-tetraazacyclododecane-N,N',N'',N'''-tetraacetic acid (DOTA); p-isothiocyanatobenzyl-1,4,7,10-tetraazacyclododecane-1,4,7,10-tetraacetic acid (p-SCN-Bz-DOTA); 1,4,7,10-tetraazacyclododecane-N,N',N''-triacetic acid (DO3A); 1,4,7,10-tetraazacyclododecane-1,4,7,10-tetrakis(2-propionic acid) (DOTMA); 3,6,9-triaza-12-oxa-3,6,9-tricarboxymethylene-10-carboxy-13-phenyl-tridecanoic acid ("B-19036"); 1,4,7-triazacyclononane-N,N',N''-triacetic acid (NOTA); 1,4,8,11-tetraazacyclotetradecane-N,N',N'', N'''-tetraacetic acid (TETA); triethylene tetraamine hexaacetic acid (TTHA); trans-1,2-diaminohexane tetraacetic acid (CYDTA); 1,4,7,10-tetraazacyclododecane-1-(2-hydroxypropyl)4,7,10-triacetic acid (HP-DO3A); trans-cyclohexane-diamine tetraacetic acid (CDTA); trans(1,2)-cyclohexane dietylene triamine pentaacetic acid (CDTPA); 1-oxa-4,7,10-triazacyclododecane-N,N',N''-triacetic acid (OTTA); 1,4,7,10-tetraazacyclododecane-1,4,7,10-tetrakis{3-(4-carboxyl)-butanoic acid}; 1,4,7,10-tetraazacyclododecane-1,4,7,10-tetrakis(acetic acid-methyl amide); 1,4,7,10-tetraazacyclododecane-1,4,7,10-tetrakis(methylene phosphonic acid); and derivatives thereof.

In some embodiments, the carboxylate-containing molecule may contain or chelate an image-enhancing moiety. Suitable image-enhancing moieties may include paramagnetic entities (e.g., transition metals and lanthanide ions) and/or entities that undergo nuclear reaction to emit a particle, such as, for example, an alpha particle, a gamma particle, a beta particle, or a positron (e.g., radioactive ions).

Illustrative examples of transition metal and lanthanide ion paramagnetic entities may include, but are not limited to: gadolinium (III), dysprosium (III), holmium (III), europium (III), iron (III), and/or manganese (II).

Illustrative radioactive ions may include, but are not limited to: actinium-225, bismuth-212, arsenic-72, indium-110, indium-111, indium-113m, gallium-67, gallium-68, strontium-83, zirconium-89, ruthenium-95, ruthenium-97, ruthenium-103, ruthenium-105, mercury-107, mercury-203, rhenium-186, rhenium-188, tellurium-121m, tellurium-122m, tellurium-125m, thulium-165, thulium-167, thulium-168, technetium-94m, technetium-99m, silver-111, platinum-197, palladium-109, copper-62, copper-64, copper-67, yttrium-86, yttrium-90, scandium-47, samarium-153, lutetium-177, rhodium-105, praseodymium-142, praseodymium-143, terbium-161, holmium-166, gold-199, cobalt-57, cobalt-58, chromium-51, iron-59, selenium-75, thallium-201, and ytterbium-169.

Carboxylate-containing molecules may contain multiple acetic acid moieties, for example, DTPA. The carboxylate-containing molecule optionally may include an amine functionality. Other exemplary carboxylate-containing molecules capable of reacting with an acid acceptor include 2-(4-carboxybenzyl)diethylenetriamine pentaacetic acid; 2-(4-carboxybenzyl)diethylenetriamine pentamethylene phosphonic acid; 2-(4-carboxybenzyl)diethylenetriamine pentamalonic acid; [(R)-2-amino-3-(4-carboxyphenyl)propyl]-trans-(S,S)-cyclohexane-1,2-diamine-pentaacetic acid; [*(R)-2-amino-3-(4-carboxyphenyl)propyl]-trans-(S,S)-cyclohexane-1,2-diamine-pentamethylene phosphonic acid; [(R)-2-amino-3-(4-carboxyphenyl)propyl]-trans-(S,S)-cyclohexane-1,2-diamine-pentamalonic acid; diethylene triamine pentaacetic acid; ethylene diamine tetraacetic acid; triethylene tetraamine hexamethylene phosphonic acid; diethylene triamine pentamethylene phosphonic acid; ethylene diamine tetramethylene phosphonic acid; triethylene tetraamine hexamalonic acid; diethylene triamine pentamalonic acid; ethylene diamine tetramalonic acid; 1,2-diaminocyclohexane-N,N,N',N'-tetraacetic acid, N,N'-di-(2-hydroxybenzyl)ethylenediamine (HBED), N-(2-hydroxyethyl)ethylenediaminetriacetic acid, nitrilotriacetic acid, ethylene-bis(oxyethylenenitrilo) tetraacetic acid (EGTA), 1,4,7,10-tetraazacyclododecane-N,N',N'',N'''-tetraacetic acid (DOTA), 1,4,7,10-tetraazacyclododecane-N,N',N''-triacetic acid (DO3A), 1,4,7-tris(carboxymethyl)-10-(2'-hydroxy)propyl)-1,4,7,10-tetraazocyclodecane (HP-DO3A), 1,4,7-triazacyclonane-N,N',N-triacetic acid (NOTA), and 1,4,8,11-tetraazacyclotetradecane-N,N',N'',N'''-tetraacetic acid (TETA).

Suitable acid acceptors for use in the invention include those that are capable of reacting with a carboxylate-containing molecule. Illustrative acid acceptors may include, but are not limited to triethylamine; trimethylamine, N,N,N',N'-tetramethylethylenediamine; N,N,N',N'-tetramethyl-1,8-napthalenediamine; N-methylmorpholine; pyridine; N,N dimethylaminopyridine; 1,5-diazobicyclo[4.3.0]non-5-ene; 1,5-diazobicyclo[5.4.0]undec-5-ene; 1,4-diazobicylo[2.2.2] octane; or 1,1,3,3-tetramethylguanidiune.

The aprotic solvent used in the disclosed methods may be any solvent capable of dissolving the carboxylate-containing molecule and acid acceptor to form the second solution. Illustrative aprotic solvents may include, but are not limited to, acetonitrile; methylene chloride; chloroform; ethylene dichloride; tetrahydrofuran (THF); 1-methyl-2-pyrrolidinone (NMP); dimethylformamide (DMF); dimethyl sulfoxide (DMSO); and derivatives of any of the foregoing. In one embodiment, the aprotic solvent is acetonitrile, which may optionally be dry, nitrogen-purged acetonitrile.

In some embodiments, a carboxylate activator is added to the carboxylate-containing molecule. Any suitable carboxylate activator can be used to activate the carboxylate-containing molecule. Illustrative carboxylate activators include, but are not limited to, acetic anhydride; butylchloroformate; isobutylchloroformate; ethylchloroformate; propylchloroformate; carbonyidiimidazole and 1,3-dicyclohexyldiimide; 1-(3-dimethylaminopropyl)-3-ethylcarbodiimide hydrohalides with or without N-hydroxysuccinamide; N-hydroxysulfosuccinamide, and phenolic coactivators; and derivatives of any of the foregoing. In a preferred embodiment, the carboxylate activator is an alkylchloroformate, such as isobutylchloroformate (IBCF).

Specific Example Using Poly(lysine) and DTPA. In one embodiment, the method of the invention entails a two-phase acetonitrile/buffer solvent system during the conjugation of DTPA to a polyamino backbone, such as poly(lysine), rather than single-phase systems. In general, a polymer salt, such as poly(lysine hydrobromide), is dissolved in a 0.1M aqueous sodium bicarbonate, 2M NaCl solution having an initial pH of about 10. DTPA and five equivalents of an acid acceptor, such as triethylamine, then may be added to the aprotic solvent, preferably dry, nitrogen-purged acetonitrile. This second solution preferably is stirred at or near 55° C. until the DTPA is dissolved. One or more carboxylate activators (e.g., IBCF) is then added to the second solution. The temperature of the second solution preferably is maintained at or near −40° C. during the addition of the carboxylate activator in order to optimize monoactivation of the DTPA. The first and second solutions are then combined into a mixture and stirred vigorously.

When the macromolecule is a polymeric salt, such as poly (lysine hydrobromide), the macromolecule is typically dissolved in a buffer solution. The buffer solution may be sodium bicarbonate (0.1M $NaHCO_3$). The initial pH of the buffer solution should range from about 9 to about 11, more preferably from about 9.5 to about 10.5, and more preferably from about 9.8 to about 10.2.

A carboxylate-containing small molecule, such as DTPA, is monoactivated using an alkyl chloroformate, such as IBCF, by reverse addition into acetonitrile (kept at or near −40° C.). The temperature of the activated DTPA-acetonitrile solution is preferably maintained at or near −40° C. during the addition of the activated DTPA in order to prevent the thermal decomposition of activated DTPA and promote a consistent degree of conjugation, in addition to preventing diactivation of DTPA that may lead to cross linking of the substituted macromolecule.

The activated DTPA-acetonitrile solution is then added to the buffer solution, for example via a pump and tubing. If the tubing is allowed to stand at ambient temperature, the residence time of activated DTPA within the tubing is preferably kept at or about 1.5 minutes or less via control of flow rate and tubing total volume. This minimizes the thermal decomposition of activated DTPA and thus promotes a consistent degree of conjugation.

In one embodiment, two or more equivalents of DTPA are used per one equivalent of poly(lysine) repeat unit to be conjugated. In other embodiments, four or more equivalents of DTPA are used per one equivalent of poly(lysine) repeat unit to be conjugated. Preferably, eight or more equivalents of DTPA are used per one equivalent of poly(lysine) repeat unit to be conjugated. This corrects for the thermal and hydrolytic decomposition of activated DTPA during conjugation to the poly(lysine). Lesser amounts of DTPA can be used to provide polymer conjugates with lower degrees of conjugation, e.g., four equivalents of DTPA under identical conditions provides about 70% conjugated material, five equivalents of DTPA provides about 92% conjugated material, six equivalents of DTPA provides about 94% conjugated material, and seven equivalents of DTPA provides about 96% conjugated material.

Vigorous stirring is applied upon addition of activated DTPA to the polymer solution in order to impede polymer cross-linking. The buffer solution of the polymer also may also contain an additive, such as sodium chloride (NaCl), to increase the buffer ionic strength. The high ionic strength leads to an aqueous/organic solvent separation and the formation of a two-phase system. Although not bound by theory, this is believed to prevent irreversible precipitation of starting materials, the poly(lysine) in particular, and improves the yield of the final product. The phase separation also may lead to a higher concentration of the reactants in the aqueous phase as compared to the single phase method used previously, which improves the rate of reaction and thus the extent of conjugation of DTPA to the poly(lysine).

The sample may optionally be purified by using known purification techniques, for example by precipitation, chromatography dialysis, ultrafiltration, or tangential flow filtration to provide high purity materials in good yield.

Imaging Methods Using the Disclosed Conjugated Macromolecules. In other embodiments, the substituted macromolecule can be used for as an imaging agent that facilitates medical imaging of a specific target (e.g., a specific organ, tissue, or other anatomical structure). The image agents produced using the disclosed methods may include moieties that generate signal (e.g., a radioactive ion) or moieties that enhance contrast (e.g., negative or positive contrast agents). In some embodiments, the image agents produced using the disclosed methods may be combined with a pharmaceutically acceptable carrier and introduced into a subject (e.g., non-human or human animal) to facilitate imaging of a specific target. The administration routes for imaging agents may include, but are not limited to, enteral (e.g., oral or rectal) and parenteral (e.g., intravenous, intramuscular, or intraperitoneal) modes of administration.

It is contemplated, for example, that the carboxylate-containing molecule can itself be a targeting agent (e.g., a small molecule, antibody or antibody fragment) to the macromolecule. It is also contemplated that a targeting agent can be attached at a few sites along the substituted polymer chain. The targeting agent can be attached to the substituted macromolecule using techniques known to those skilled in the art. It is also contemplated that targeting agents can be used in combination with other types of active agents incorporated into the substituted macromolecule.

Thus, for example, the substituted macromolecule can be highly conjugated with a non-targeting carboxylate-containing molecule that chelates an image producing entity and a targeting agent can appear at only a few sites along the backbone. As another example, the macromolecular backbone can be highly conjugated with a non-targeting carboxylate-containing molecule, and a targeting agent can be bound to the carboxylate-containing molecule, rather than being bound directly to the substituted macromolecule.

EXAMPLES

Unless otherwise indicated, the following materials and methods were used in the examples that follow. Poly(allylamine), poly(allylamine hydrochloride), poly(lysine), poly(lysine-glutamic acid), poly(lysine-serine), diethylenetriaminepentaacetic acid (>99%), isobutylchloroformate (>99%), triethylamine (>99%), 1-(3-dimethylaminopropyl)-3-ethylcarbodiimide (Aldrich) and trinitrobenzene sulfonic acid (TNBSA, Pierce) were used as received; acetonitrile was distilled over $CaH_2$; 18Ω water was obtained from a Millipore four-stage filtration device. All reactions were performed on a Schlenk line under an $N_2$ inert atmosphere unless otherwise stated using glassware that had been pre-rinsed with 18MΩ water. Prior to use for material purification, 5 KDa and 10 KDa MWCO ultrafilters (Amicon) were pre-rinsed with 18MΩ water at 4000 rpm on a centrifuge (Sorvall RC-5B Superspeed Centrifuge, equipped with swinging bucket rotor). HPLC analysis was performed using a Dionex LC25 chromatography oven fitted with an Agilent Zorbax GF250 column, an AD25 absorbance detector and a GP40 gradient pump eluting with a potassium phosphate buffer (pH 7, 20 mM, 165 mM NaCl).

Manual reagent manipulations were performed using 500 μL and 10 mL gastight syringes. Pump delivery of isobutylchloroformate (IBCF) solutions used Fischer Scientific Variable Flow Peristaltic Pumps (No. 13876) equipped with silicone tubing at the pump head rotor and Teflon inlet and outlet tubing reinforced with Masterflex Pharmed tubing or electrical tape at tubing junctions where necessary. The Teflon inlet was attached to an $N_2$ pressurized addition funnel containing the IBCF solution and sealed with parafilm and a Pharmed tubing adapter if necessary. The Teflon pump outlet tubing was inserted into the DTPA reagent via a pierced septum attached to one neck of the DTPA reactor. Activated DTPA transfer employed the same pump delivery system described above for small scale reactions and a Masterflex L/S pump (No. 7550-20) equipped with a Masterflex L/S pump head (No. 7518-60) using Masterflex Pharmed tubing, modified with Teflon tubing inlet and outlet terminal inserts. The inlet tubing was inserted into the activated DTPA reaction mixture via pierced septum attachment to one reactor neck. The pump outlet tubing was then inserted into the poly(allylamine) single neck flask reactor (equipped with a stirrer) through a pierced septum also vented with a 50-gauge needle attached to a Schlenk line. The outlet tubing was held above the macromolecule reaction mixture to permit dropwise reagent addition. A ThermoNeslabs CC-65 cooling unit, equipped with a ThermoNeslabs Cryotrol temperature controller was used to control the DTPA reactor temperature during IBCF addition. The reactor was placed in a Dewar flask containing isopropyl alcohol cooling bath, the cooling finger and an alcohol thermometer for small-scale reactions. For larger scale procedures, a plastic tub insulated with rubber foam was used as to hold the IPA cooling solution and 3 L three neck DTPA reactor. The activated DTPA slurry was stirred at ~75 rpm using a mechanical stirrer and macromolecule solution stirred with a magnetic stirrer.

Determination of Percentage Conjugation: the percentage conjugation refers to the percentage of free amine functional groups within an amine-containing macromolecule that are conjugated with a carboxylate containing molecule to afford a substituted macromolecule. In the case of DTPAGd substituted macromolecules, the percentage conjugation is determined as:

[Gd]/[Gd]+[NH2]

where [Gd]=concentration of gadolinium as determined by ICP-AES. [NH$_2$]=concentration of free amine functional groups as determined by calorimetric assay.

ICP Measurement: the concentration of gadolinium in a given analyte was determined in triplicate using a Varian Liberty II ICP-AES instrument. Two lines were monitored for each element, where both lines agreed within the 95% confidence intervals according to the following method:

TABLE 1

| Pump Rate | |
| --- | --- |
| Pump Rate: 15 rpm | PMT Voltage: 700 V |
| Snout: On | Plasma Gas: 15.0 L/min |
| Auxiliary Gas: 1.50 L/min | Sample Uptake: 30 sec |
| Fast Pump: On | Rinse Time: 60 sec |
| Smart Rinse: None | |

The analyte concentrations were calculated by comparison with a known series of single element external calibration standards prepared wt/volume for 10, 5, 2, 1, 0.5, 0.2 and 0.1 ppm in 12.5% HNO3, containing 1 ppm Sc as internal standard. Samples were prepared as aqueous solutions, approximately 100 in volume prepared in microwave vessel along with blank (1 ml of 18M water) and spike (1 ml of 100 ppm Gd in 1% $HNO_3$) control samples. The analyte samples are dissolved in 2.5 ml of Ultrex $HNO_3$, 1.5 mL $H_2O$, 1 mL $H_2O_2$, and heated by microwave as follows:

TABLE 2

| | Heating Program: Ramp to Temperature | | | | | |
| --- | --- | --- | --- | --- | --- | --- |
| Stage | Max. Power | % Power | Ramp (min.) | Pressure (psi) | T (° C.) | Hold (min.) |
| (1) | 1200 W | 100 | 15.00 | 20 | 120 | 5.00 |
| (2) | 1200 W | 100 | 15.00 | 40 | 140 | 5.00 |
| (3) | 1200 W | 100 | 15.00 | 55 | 160 | 5.00 |
| (4) | 1200 W | 100 | 15.00 | 100 | 165 | 5.00 |

When the heating program was completed, the vessels were allowed to cool and 2 mL of a 10 ppm Sc internal standard added; 18 MΩ water was then added to bring the final volume of 20 ml. Free amine concentrations of the analyte samples were determined in triplicate by calorimetric titration using a 96-well plate that also contained triplicate N-α-acetyl-L-lysine standards ranging in concentration from 25 to 300 mm and a 18 MW 0.1 M sodium bicarbonate, pH 9.0 blank. Analyte samples were diluted in fresh 0.1 M sodium bicarbonate, pH 9.0, to ~150 mm free amine concentration. A 0.01% by volume TNBSA in 0.1 M sodium bicarbonate, pH 9.0 aliquot was then added to the analyte and standards and the mixtures heated at 37° C. for two hours. The solutions were then quenched with 50 mL of 0.33 M HCl and the absorbances determined using a Becton Dickinson Microtest™ 96 or Molecular Devices Spectra Max M2 absorbance detector.

Example 1

Synthesis of PAA-GdDTPA, 97% Conjugation.
(Automated Reagent Addition)

A sample of DTPA (6.76 g, 17.4 mmol) and acetonitrile (46 mL) was degassed for 20 minutes. Upon addition of $NEt_3$ (12.40 ml, 87.8 mmol), the reaction mixture was heated to 60° C. for 1 hr with stirring. The resultant clear, colorless solution was then transferred by syringe to a three-necked flask, equipped with a mechanical stirrer, and cooled to about −40° C. An acetonitrile solution (23 mL) of isochlorobutylformate (ICBF) (2.5 mL, 19.4 mmol) was then added to the reaction mixture at a rate of 1.8 ml/min over the course of 14 mins. The reaction mixture was allowed to stir for 1 hour at −45° C. resulting in the gradual formation of a white precipitate at which point stirring was halted. Under an inert atmosphere, one neck of the reactor was equipped with a septum fitted with a Teflon tube that was inserted into the reaction mixture. The activated DTPA reagent was maintained at −40° C., and then pumped (5.0 ml/min, 18 minutes) to a second reactor containing a clear, colorless aqueous $NaHCO_3$ (0.1M, pH 10)/ NaCl (2M, 2.69 g, 46 mmol) solution (23 mL) of poly(allylamine.HCl) (56 mg, 0.6 mmol $M_w$=15 KDa, DP=160) at ambient temperature. The resulting cloudy biphasic reaction mixture was stirred vigorously in a baffled reactor for 16 hours at which point stirring was stopped, the reaction mixture transferred to a separatory funnel and then allowed to settle into two phases. The lower cloudy aqueous layer was separated and added to an aqueous $NaHCO_3$ (0.1M, pH 10)/ NaCl (2M, 2.69 g, 46 mmol) solution (23 mL) to afford a colorless solution of the crude product that was then purified by ultrafiltration (Amicon Ultrafilters, 10K MWCO), washing with distilled water (6×10 mL).

The product was analyzed by HPLC to confirm removal of low Mw byproducts and then directly added to a Gdcitrate (50 mM Gd, 125 mM $Na_3$Citrate) solution (50 mL, 2.5 mmol Gd) to provide a clear colorless solution that was stirred for 16 hours. The crude reaction mixture was purified by ultrafiltration (Amicon Ultrafilters, 10K MWCO), washing with distilled water (6×10 mL), to provide a clear colorless solution of PAA-GdDTPA, 52% yield, >99% purity (HPLC), 97% conjugation.

Example 2

Synthesis of PAA-GdDTPA, 68% Conjugation. (Automated Reagent Addition)

A sample of DTPA (3.38 g, 8.7 mmol) and acetonitrile (46 mL) was degassed for 20 minutes. Upon addition of $NEt_3$ (6.20 ml, 43.9 mmol), the reaction mixture was heated to 60° C. for 1 hour with stirring. The resultant clear, colorless solution was then transferred by syringe to a three-necked flask, equipped with a mechanical stirrer, and cooled to −40° C. An acetonitrile solution (23 mL) of IBCF (1.25 mL, 9.7 mmol) was then added to the reaction mixture at a rate of 2.4 ml/min over the course of 10 minutes. The reaction mixture stirs for 1 hour at about −45° C., resulting in the gradual formation of a white precipitate at which point stirring was halted. Under an inert atmosphere, one neck of the reactor was equipped with a septum fitted with a Teflon tube that was inserted into the reaction mixture. The activated DTPA reagent was maintained at −40° C., and then pumped (5.3 ml.min-1, 15 mins) to a second reactor containing a clear, colorless aqueous $NaHCO_3$ (0.1M, pH 10)/NaCl (2M, 2.69 g, 46 mmol) solution (23 mL) of poly(allylamine) (0.6 g 20 wgt % water solution, 0.6 mmol, $M_w$=17 KDa, DP=300) at ambient temperature. The resulting cloudy biphasic reaction mixture was stirred vigorously in a baffled reactor for 16 hours at which point stirring was stopped, the reaction mixture transferred to a separatory funnel and allowed to settle into two phases. The lower cloudy aqueous layer was separated and added to an aqueous $NaHCO_3$ (0.1M, pH 10)/NaCl (2M, 2.69 g, 46 mmol) solution (23 mL) to afford a colorless, slightly cloudy solution of the crude product which was then centrifuged (3000 rpm) to pelletize the solids. Decantation isolated the pellet and provided a clear colorless solution of the crude product that was then purified by ultrafiltration (Amicon Ultrafilters, 10K MWCO), washing with distilled water (6×10 mL).

The product was analyzed by HPLC to confirm removal of low molecular weight by-products and then directly added to a Gdcitrate (50 mM Gd, 125 mM $Na_3$Citrate) solution (60 mL, 3.0 mmol Gd) to provide a clear colorless solution that was stirred for 16 hours. The crude reaction mixture was purified by ultrafiltration (Amicon Ultrafilters, 10K MWCO), washing with distilled water (6×10 mL), to provide a clear colorless solution of PAA-GdDTPA, 42% yield, >99% purity (HPLC), 68% conjugation.

Example 3

Synthesis of Poly(Lysine-DTPA) (Manual Addition)

A flask was charged with DTPA (3.38 g, 8.7 mmol), triethylamine (6.2 mL, 43.9 mmol) and acetonitrile (46 mL), and degassed for 15 minutes, resulting in a cloudy solution. The reaction mixture was then stirred at 55° C. for 1 hour, generating a clear colorless solution, and then transferred to a three-necked flask equipped with a mechanical stirrer and cooled to about −40° C. An acetonitrile (23 mL) solution of isobutylchloroformate (1.25 mL, 9.7 mmol) was then added dropwise by syringe to the cooled reaction mixture over 18 minutes and the solution was stirred for 1 hour.

The resulting slurry was decanted dropwise into a 0.1 M sodium bicarbonate, 2M sodium chloride buffer solution (pH=10) of poly(lysine hydrobromide) (0.25 g, 1.2 mmol, DP 277, Mw=58,000) over the course of 14 minutes, with vigorous stirring, to produce an opaque biphasic reaction mixture that was stirred for 12 hours at ambient temperature. The reaction mixture was transferred to a separatory funnel and the lower aqueous layer was then added to 23 mL of a 0.1 M sodium bicarbonate, 2 M sodium chloride buffer solution (pH=10) to provide a clear colorless solution.

The crude reaction mixture was purified by tangential flow filtration (Pall Corporation suspended screen channel 30K MWCO, $NaHCO_3$ (pH=7) purification stream) to afford a clear colorless solution of poly(lysine-DTPA)0.97-ran-(lysine)0.03 in 67% yield and with greater than 96% purity.

Example 4

Synthesis of Poly(Lysine-DTPA) (Automated Reagent Addition)

A sample of DTPA (3.38 g, 8.7 mmol) and acetonitrile (46 mL) was degassed for 20 minutes. Upon addition of NEt3 (6.20 ml, 43.9 mmol), the reaction mixture was heated to 60° C. for 1 hour with stirring. The resultant clear, colorless solution was then transferred by syringe to a three-necked flask, equipped with a mechanical stirrer and cooled to −40° C. An acetonitrile solution (23 mL) of i-BuCOCl (1.25 mL, 9.7 mmol) was then added to the reaction mixture at a rate of 1.2 ml.min$^{-1}$ over the course of 20 minutes. The reaction mixture was allowed to stir for 1 hour at −45° C., resulting in the gradual formation of a white precipitate at which point stirring was halted.

Under an inert atmosphere, one neck of the reactor was equipped with a septum fitted with a Teflon tube that was inserted into the reaction mixture. The DTPA reagent was maintained at −40° C., and then pumped (4.4 ml.min$^{-1}$ for 17 minutes) to a second reactor containing a clear, colorless aqueous NaHCO$_3$ (0.1 M, pH 10)/NaCl (2 M, 2.69 g, 46 mmol) solution (23 mL) of poly(lysine) (0.25 g, 1.2 mmol M$_w$=84,000 g.mol-1, DP=402) at ambient temperature. The resulting cloudy biphasic reaction mixture stirred vigorously in a baffled reactor for 16 hours at which point stirring was stopped, the reaction mixture transferred to a separatory funnel and then allowed to settle into two clear colorless phases. The lower aqueous layer was separated and added to an aqueous NaHCO$_3$ (0.1 M, pH 10)/NaCl (2 M, 2.69 g, 46 mmol) solution (23 mL) to afford a clear colorless solution of the crude product.

The crude reaction mixture was purified by ultrafiltration (4× Amicon Ultrafilters, 10K MWCO, 2000 rpm), and washed with five cycles of distilled water (4×12 mL, 18MΩ) to remove low Mw byproducts, as verified by GPC, providing the product Poly(lysine-DTPA) as a clear colorless DI solution, in an 84% yield, with a 98% purity (HPLC) and 97±1.4% conjugation, Mw (MALLS)=208 KDa.

Example 5

Direct Gadolinium Labeling of Poly(Lysine-DTPA) in the Synthesis of Poly(Lysine-DTPA-Gd)

Figure 2:
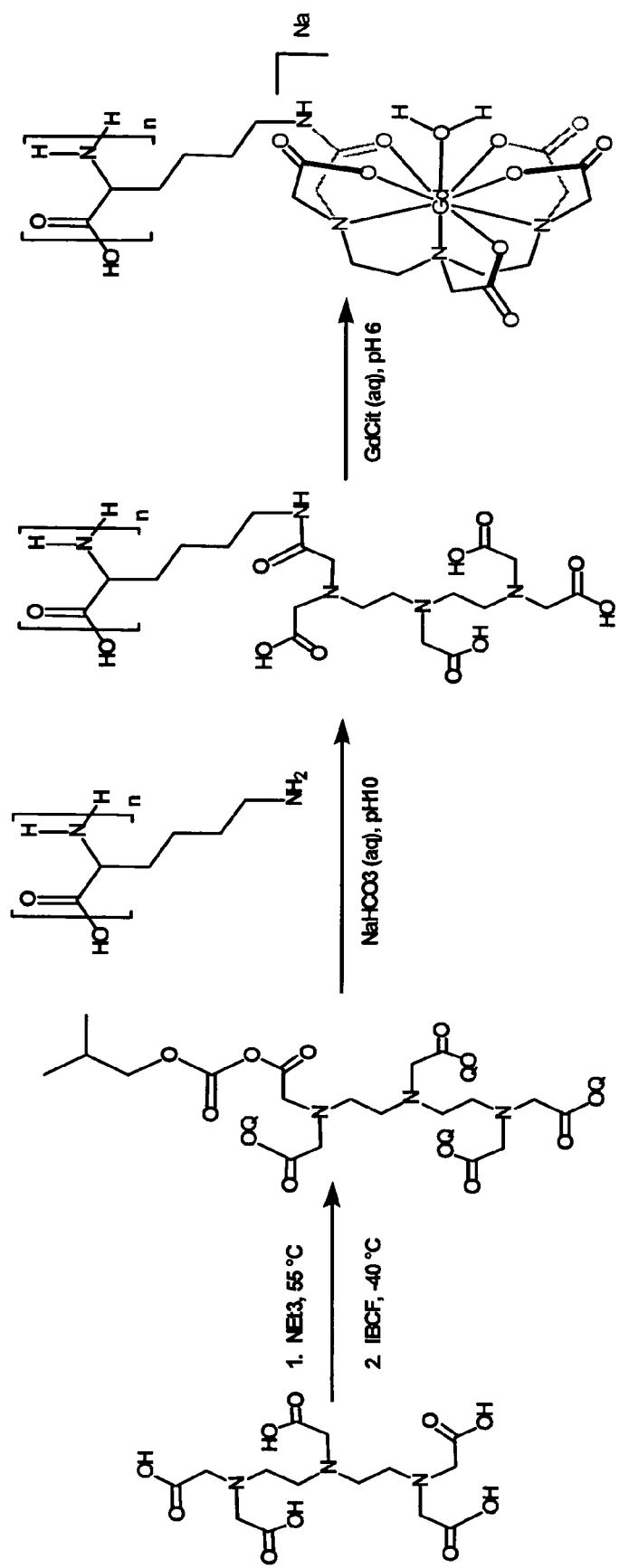
FIG. 2 depicts the activation of the chelator DTPA to provide an activated DTPA, which is then conjugated to the N amine functional group contained within the repeat unit of poly(lysine) to form the substituted macromolecule poly(lysine-DTPA). The substituted macromolecule, poly(lysine-DTPA), is then labeled with gadolinium to afford the poly(lysine-DTPA-Gd).

The crude product from Example 2 was treated with GdCitrate (44 mL, 0.3 M) and allowed to stir at ambient temperature for 16 hours. The crude reaction mixture was then concentrated to 40 mL volume by ultrafiltration (4× Amicon Ultrafilters, 10K MWCO, 2000 rpm), and washed with five cycles of distilled water (4×12 mL, 18MΩ) to remove low molecular weight by-products, as verified by GPC, providing the product Poly(lysine-DTPA-Gd) as a clear colorless DI solution, in a 71% overall yield, with 99% purity (GPC) and 97±1.4% conjugation, MW (MALLS)=270 KDa. (See, e.g., FIG. 2.)

Example 6

Single Phase Synthesis of Poly(Lysine-DTPA-Gd) (Manual Addition)—Control Experiment A flask was charged with DTPA (3.38 g, 8.7 mmol), triethylamine (6.2 mL, 43.9 mmol) and acetonitrile (46 mL), and degassed for 15 minutes, resulting in a cloudy solution. The reaction mixture was then stirred at 55° C. for 1 hour, generating a clear colorless solution, and then transferred to a three-necked flask equipped with a mechanical stirrer and cooled to about −40° C. An acetonitrile (23 mL) solution of isobutylchloroformate (1.25 mL, 9.7 mmol) was then added dropwise by syringe to the cooled reaction mixture over 18 minutes and the solution was stirred for 1 hour.

The resulting slurry was added dropwise into a 0.1 M sodium bicarbonate buffer solution (23 mL, pH=10) of poly (lysine hydrobromide) (0.25 g, 1.2 mmol, M$_w$=84 KDa, DP=402) over the course of 14 minutes and the reaction mixture vigorously stirred for 12 hours. The crude reaction mixture contained a precipitate and was transferred into two centrifuge tubes and centrifuged at 200 rpm for 30 minutes to pelletize the precipitate. A clear colorless solution was decanted from the resulting gelatinous pellet, labeled with GdCitrate (44 mL, 0.3M) and allowed to stir at ambient temperature for 12 hours. The crude reaction mixture was then concentrated to 40 mL volume by ultrafiltration (4× Amicon Ultrafilters, 10K MWCO, 2000 rpm), and washed with five cycles of distilled water (4×12 mL, 18MΩ) to remove low molecular weight by-products, as verified by GPC, providing the product Poly(lysine-DTPA-Gd) as a clear colorless DI solution, in a 29% yield, with 99% purity (GPC) and 97±1.4% conjugation, MW (MALLS)=270 KDa.

Example 7

Effect of Residence Time and Storage Temperature on Poly(Lysine-DTPA) Degree of Conjugation Initial experiments to optimize the degree of poly(lysine-DTPA) conjugation were conducted manually on a small scale to provide highly conjugated poly(lysine-DTPA) i.e. >90% DTPA conjugation of the lysine residues. This process involved manual syringe addition of IBCF to produce the activated DTPA intermediate and manual decanting of activated DTPA to afford highly conjugated poly(lysine-DTPA), as shown in Table 3. For the purposes of reproducibly controlling reagent addition rates at larger reaction scales, a series of pumps were then implemented and the effects of pumped reagent delivery on degree of conjugation characterized at a small scale for later transition to larger scales. The study of pump controlled reagent addition revealed that the degree of poly(lysine-DTPA) conjugation was dependant on both the storage temperature and tubing residence time of the activated DTPA. In an attempt to mimic manual addition experimental conditions, the first experiment involving IBCF and DTPA pump delivery did not involve the maintenance of activated DTPA storage temperature at about −40° C. and used a flow rate of 1.4 ml.min$^{-1}$ for the addition of activated DTPA.

These conditions produced lower conjugation poly(lysine-DTPA) than that observed in the approximated analogous manual addition experiments, even though an extra equivalent of DTPA was used. As shown in Table 3, a sample with 70% conjugation was obtained when the activated DTPA reagent was not kept at about −40° C. during its transfer; this followed the manual activated DTPA addition method where the cooling bath was also removed during the decanting of the reagent. When the experiment was repeated and the activated DTPA storage temperature was maintained at about −40° C., the degree of conjugation improved to 81% of the available lysines. This was an improvement that still did not afford greater than 90% lysine conjugation obtained manually, but illustrated the thermally sensitive nature of DTPA and the need to control the activated DTPA storage temperature in order to reproducibly optimize the degree of conjugation.

Although stored at about −40° C. prior to transferal by pump, the activated DTPA lifetime in the minimal amount of Teflon tubing used was too short to facilitate satisfactory DTPA conjugation of poly(lysine) (>90%) and indicated that the activated DTPA tubing residence time, under the ambient temperature during transfer, was too long. Accordingly, the flow rate of activated DTPA transfer was then approximately doubled, thereby halving the tubing residence time at ambient temperature, to reduce the activated DTPA decomposition; a modification that afforded the poly(lysine-DTPA) product with 98% conjugation under otherwise identical conditions as shown in Table 3. Furthermore, the number of equivalents of DTPA used for conjugation of the macromolecule could be reduced from seven to four equivalents by increasing the flow rate of the activated DTPA by decreasing the ambient temperature residence time, as shown in Table 3. By increasing the activated DTPA flow rate from 2.7 to 7.0 mL.min-1, four equivalents of DTPA could be employed to synthesize poly (lysine-DTPA) with 98% conjugation.

TABLE 3

DTPA Addition

| Run | IBCF Addition Mode | Poly (lysine-DTPA) | Mode | Rate (ml · min − 1) | Storage Temp. (° C.) | Conj. (%) |
|---|---|---|---|---|---|---|
| BG1-86 | Manual | 6 | Manual | 1.8 | — | 93 |
| BG1-87 | Manual | 6 | Manual | 1.8 | — | 96 |
| BG1-88 | Pump | 7 | Pump | 1.4 | Ambient | 70 |
| BG1-92 | Pump | 7 | Pump | 1.5 | −40 | 81 |
| BG1-93 | Pump | 7 | Pump | 2.7 | −40 | 98 |
| EW4928 | Pump | 4 | Pump | 7 | −40 | 96 |

Figure 3:
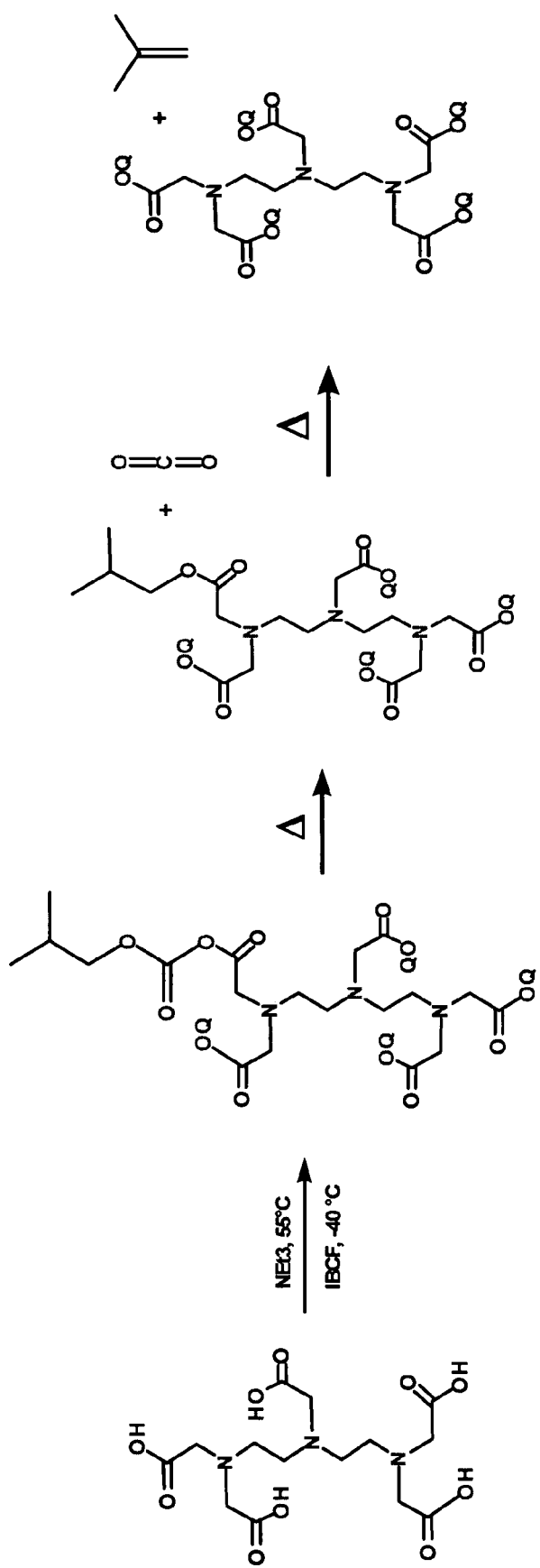
FIG. 3 depicts a proposed mechanism for the thermal decomposition of the activated DTPA, DTPA-isobutylcarbonic anhydride.

The thermal sensitivity of the DTPA reagent was investigated by the generation and attempted isolation of a sample of DTPA. Characterization of the crude reaction mixture by NMR spectroscopy revealed that DTPA was predominantly recovered with trace amounts of mono- and di-isobutyl ester of DTPA according to mass spectroscopy. This suggested that thermal decarbonylation of DTPA, presumably followed by isobutylene elimination, as a likely mechanism of DTPA decomposition (See, e.g., FIG. 3).

The study taught that the degree of conjugation of the substituted macromolecule, such as poly(lysine-DTPA) was dependant on the storage temperature and residence time of the reactive intermediates that are subject to decomposition, such as activated DTPA. By controlling parameters that affect the extent of activated carboxylate containing molecule decomposition, the degree of conjugation of the could ultimately be controlled, Accordingly, short residence times (e.g., less than 2 minutes) should be used when adding activated DTPA to poly(lysine) solutions. To further prevent or minimize the detrimental effects of decomposition, the activated DTPA solution should be maintained cool (e.g., at or near −40° C.) during the addition of activated DTPA.

When increasing the scale of the conjugation reaction the effects of storage temperature and residence time were considered. The tubing volumes and addition times for both IBCF and activated DTPA addition phases were collected to calculate the residence times at a 1 g scale, where the flow rates were known. Subsequently, the tubing volume and flow rate during the transferal of the activated DTPA for a 5 g scale of poly(lysine) could then be adjusted to recreate the same residence time as used in the fully validated smaller 1 g scale reaction, as shown in Table 4. Thus, when the storage temperature and residence time of the activated DTPA were maintained during the 5 g scale-up process, the conjugation reaction successfully provided poly(lysine-DTPA) with 98% conjugation.

TABLE 4

Scaling of Reagent Flow Rate and Tubing

| Volume · Scale | Tube Vol. (mL) | Min. Flow Rate (mL · min − 1) | Residence Time (min.) |
|---|---|---|---|
| DTPA (1 g) | 9.9 | 6.5 | 1.5 |
| DTPA (5 g) | 21 | 13.8 | 1.5 |
| IBCF (1 g) | 6.3 | 1.2 | 5.3 |
| IBCF (5 g) | 9.9 | 1.9 | 5.3 |

Table 5 illustrates the tendency of water-soluble macromolecules, such as poly(lysine), to precipitate from solvent systems that consist of both aqueous and miscible polar organic components as a single solvent phase. The addition of differing volumes of acetonitrile, acetone or methylene chloride to an aqueous pH 10 solution of poly(lysine), for example, lead to the precipitation of the macromolecule as a white material that could not be redissolved into an aqueous solution upon isolation. Thus conjugation reactions involving such two component aqueous/polar organic systems would lead to irreversible precipitation of the macromolecular starting material and a dramatic loss in yield of the substituted macromolecular product.

In contrast, when the same aqueous macromolecular solution contained a 2M NaCl additive and was mixed with various polar organic solvents, the two solvents were immiscible and separated into two phases thereby preventing the precipitation of poly(lysine). Thus activation chemistry of carboxylate containing molecules that require the use of polar organic solvents prior to conjugation with aqueous solutions of macromolecules may proceed in higher yield when a two phase solvent system is induced to prevent precipitation of the macromolecular starting material.

TABLE 5

Solubility of Poly(lysine) in Mixed Aqueous and Organic Solvent Systems

| Aqueous Solution | Solvent | No. of Phases | Precipitation | Vol. % Solvent for Macromolecule Precipitation |
|---|---|---|---|---|
| 0.1M NaHCO₃ | acetonitrile | 1 | Yes | 33 |
| 0.049M poly(lysine) | acetone | 1 | Yes | 50 |
| | methylene chloride | 1 | Yes | 50 |
| 0.1M NaHCO₃ 2M NaCl | acetonitrile | 2 | No | — |
| | acetone | 2 | No | — |
| 0.049M poly(lysine) | methylene chloride | 2 | No | — |

This new biphasic conjugation method was employed in the synthesis of highly conjugated poly(lysine-DTPA) where an acetonitrile solution of activated DTPA was mixed with a 2M NaCl pH10 solution of poly(lysine) to generate a biphasic reaction mixture and compared to the use of a pH10 solution of poly(lysine), without 2M NaCl, which led to the formation of a two solvent single phase reaction mixture. When the reaction was carried out in an aqueous/polar organic single phase, the poly(lysine) had low solubility in the solvent combination and precipitated out irreversibly. This decreased the amount of polymer starting material available in solution and thereby reduced the yields of the poly(lysine-DTPA) product to 29%. By inducing the formation of the corresponding multiphasic solvent system, one aqueous for the polymer and another polar organic for the hydrolytically sensitive carboxylate organic moiety (e.g. activated DTPA), the polymer was not exposed to the organic conditions and did not precipitate from solution. This culminated in a much higher poly(lysine-DTPA) product yield of 78% with no loss in degree of conjugation (98%). Additives, such as NaCl (2M), may be employed to separate the CH₃CN and H₂O layers into a multiphase solvent system, but any additive that increases ionic strength may be used, such as other salts, to cause phase separation. Organic and aqueous solvent mixtures that are immiscible under ambient conditions or otherwise naturally produce multiphase solvent systems and may also be used.

TABLE 6

Effects of Two-Phase Solvent System
on Poly(lysine-DTPA-Gd) Yield

| Reaction Phase | % Conjugation | % Yield Poly(lysine-DTPA-Gd) |
|---|---|---|
| Single-Phase (CH3CN/pH 10 0.1M Buffer) | 95 ± 1 | 29 ± 11 |
| Two-Phase (CH3CN/ 2M NaCl pH 10 0.1M buffer) | 98 ± 1 | 78 ± 11 |

The utility of this conjugation method towards a macromolecule of different molecular weights and different types of amine-containing macromolecules was explored, as summarized in Tables 6 and 7, respectively. The process was used to make a series of poly(lysine-DTPA-Gd) constructs with various degrees of polymerization (DP) ranging from 100 to 505 repeat units. The methodology could be used to afford highly conjugated poly(lysine-DTPA-Gd)(97%-100%) in good to excellent yield (62% -94%) regardless of the starting material DP, thereby illustrating the utility of the conjugation method towards macromolecules with a wide range of molecular weights.

TABLE 7

Effect of Molecular Weight on Biphasic
Synthesis of Poly(lysine-DTPA-Gd)

| % Conjugation | Sample | DP | Yield |
|---|---|---|---|
| 97 | ew040817 | 135 | 94 |
| 97 | ew040913 | 402 | 81 |
| 97 | bg2-32 | 230 | 62 |
| 100 | bg2-35 | 100 | 76 |
| 99 | bg2-36 | 402 | 82 |
| 99 | bg2-37 | 505 | 70 |
| 98.2 | Average | | 77.5 |
| 1.3 | Standard Deviation | | 11.0 |

The application of this biphasic synthetic method towards other amine containing macromolecules was also explored. As shown in Table 8, several polypeptides containing lysine repeat units were conjugated with DTPA in addition to the synthetic macromolecule poly(allylamine). In all cases, highly conjugated (96%-99%) macromolecular constructs were obtained in good to excellent yields and the successful application of this procedure for the conjugation of carboxylate containing molecules to other amine-containing macromolecules is anticipated.

TABLE 8

DTPA Conjugation to Macromolecules

| Macromolecule | Equiv. DTPA | pH | Conjugation(%) | Yield (%) |
|---|---|---|---|---|
| Poly(lysine) | 6 | 10 | 97 | 81 |
| Poly(lysine)-(glutamic acid) | 6 | 10 | 99 | 71 |
| Poly(lysine)-(serine) | 6 | 10 | 96 | 83 |
| Poly(allylamine) | 29 | 10 | 97 | 55 |

Synthesis of BSA-DTPAGd. A sample of DTPA (3.38 g, 8.7 mmol) and acetonitrile (46 mL) is degassed for 20 minutes. Upon addition of NEt3 (6.20 ml, 43.9 mmol), the reaction mixture is heated to 60° C. for 1 hour with stirring. The resultant clear, colorless solution is then transferred by syringe to a three-necked flask, equipped with a mechanical stirrer and cooled to −40° C. An acetonitrile solution (23 mL) of i-BuCOCl (1.25 mL, 9.7 mmol) is then added to the reaction mixture at a rate of 1.2 ml.min$^{-1}$ over the course of 20 minutes. The reaction mixture is allowed to stir for 1 hr at −45° C., resulting in the gradual formation of a white precipitate at which point stirring is halted.

Under an inert atmosphere, one neck of the reactor is equipped with a septum fitted with a Teflon tube that is inserted into the reaction mixture. The DTPA reagent is maintained at −40° C., and then pumped (4.4 ml.min$^{-1}$ for 17 minutes) to a second reactor containing a clear, colorless aqueous NaHCO$_3$ (0.1 M, pH 10)/NaCl (2 M, 2.69 g, 46 mmol) solution (23 mL) of BSA (1.25 g, ~1.2 mmol lysines $M_w$=66 KDa) at ambient temperature. The resulting cloudy biphasic reaction mixture is stirred vigorously in a baffled reactor for 16 hrs at which point stirring is stopped, the reaction mixture is transferred to a separatory funnel and then allowed to settle into two clear colorless phases. The lower aqueous layer is separated and added to an aqueous NaHCO$_3$ (0.1 M, pH 10)/NaCl (2 M, 2.69 g, 46 mmol) solution (23 mL) to afford a clear colorless solution of the crude product. The crude reaction mixture is treated with GdCitrate (44 mL, 0.3 M) and allowed to stir at ambient temperature for 16 hours. The crude reaction mixture is then concentrated to 40 mL volume by ultrafiltration (4× Amicon Ultrafilters, 10K MWCO, 2000 rpm), and washed with five cycles of distilled water (4×12 mL, 18MΩ) to remove low molecular weight by-products, as verified by GPC, providing the product BSA-DTPA-Gd as a clear colorless DI solution.

While specific embodiments of the invention have been illustrated and described herein, it should be appreciated that modifications and changes will occur to those skilled in the art. It is therefore to be understood that the appended claims are intended to cover all such modifications and changes as fall within the spirit and scope of the invention.

We claim:

1. A method of conjugating a carboxylate-containing molecule to an amine-containing macromolecule in a multiphasic solution to form a substituted macromolecule comprising:
    (a) forming a first solution by dissolving at least one amine-containing macromolecule in an aqueous basic solution;
    (b) forming a second solution by combining at least one carboxylate-containing molecule with at least one acid acceptor in an aprotic organic solvent;
    (c) adding at least one carboxylate-activating agent to the second solution to form an activated carboxylate-containing molecule;
    (d) generating a multiphasic solution by mixing the first solution and the second solution in the presence of sodium chloride, wherein the sodium chloride is present at a concentration of 2 molar; and
    (e) forming the substituted macromolecule in the multiphasic solution.

2. The method of claim 1, wherein the second solution is maintained at a temperature below about −40° C.

3. The method of claim 1, wherein the first solution is an aqueous basic solution with an initial pH in the range from about 9 to about 12.

4. The method of claim 3, wherein the aqueous basic solution is an aqueous sodium bicarbonate solution with an initial pH in the range from about 9 to about 10.

5. The method of claim 1, wherein both the first solution and the second solution is miscible under ambient reaction conditions.

6. The method of claim 1, wherein the at least one carboxylate-containing molecule includes a metal chelator.

7. The method of claim 6, wherein the metal chelator is selected from the group consisting of DTPA, EDTA, DOTA, p-SCN-Bz-DOTA, DO3A, DOTMA, B-19036, NOTA, TETA, TTHA, CYDTA, HP-DO3A, CDTA, CDTPA, OTTA, and combinations thereof.

8. The method of claim 6, wherein the carboxylate-containing molecule comprises at least one radioactive ion.

9. The method of claim 8, wherein the radioactive ion is selected from the group consisting of actinium-225, bismuth-212, arsenic-72, indium-110, indium-111, indium-113m, gallium-67, gallium-68, strontium-83, zirconium-89, ruthenium-95, ruthenium-97, ruthenium-103, ruthenium-105, mercury-107, mercury-203, rhenium-186, rhenium-188, tellurium-121m, tellurium-122m, tellurium-125m, thulium-165, thulium-167, thulium-168, technetium-94m, technetium-99m, silver-111, platinum-197, palladium-109, copper-62, copper-64, copper-67, yttrium-86, yttrium-90, scandium-47, samarium-153, lutetium-177, rhodium-105, praseodymium-142, praseodymium-143, terbium-161, holmium-166, gold-199, cobalt-57, cobalt-58, chromium-51, iron-59, selenium-75, thallium-201, ytterbium-169, and combinations thereof.

10. The method of claim 1, wherein the carboxylate activating agent is selected from the group consisting of alkylchloroformates, EDC, DCC, CDI, EDC/NHS, DCC/HNS, EDC/NHSOSu, DCC/NHSOSu, phenolic coactivators, and combinations thereof.

11. The method of claim 1, wherein the carboxylate-activating agent comprises isobutylchloroformate.

12. The method of claim 1, wherein the at least one acid acceptor is selected from the group consisting of triethylamine, trimethylamine, N,N,N',N'-tetramethylethylenediamine, N,N,N',N'-tetramethyl-1,8-napthalenediamine, N-methylmorpholine, pyridine, N,N-dimethylaminopyridine, 1,5-diazobicyclo[4.3.0]non-5-ene, 1,5-diazobicyclo[5.4.0]undec-5-ene, 1,4-diazobicylo[2.2.2]octane, 1,1,3,3-tetramethylguanidiune, and combinations thereof.

13. The method of claim 12, wherein the at least one acid acceptor comprises triethylamine.

14. The method of claim 1, wherein the aprotic solvent is selected from the group consisting of acetonitrile, methylene chloride, chloroform, ethylene dichloride, tetrahydrofuran, 1-methyl-2-pyrrolidinone, dimethylformamide, dimethyl sulfoxide, and combinations thereof.

15. The method of claim 14, wherein the aprotic solvent comprises acetonitrile.

16. The method of claim 1, wherein the amine-containing macromolecule is selected from the group consisting of polymeric amino acids, glycosylated polymeric aminoacids, amino sugars, hormones, antibiotics, aminated carbohydrates, cofactors, aminated dendrimers, aminated nanoparticles, and combinations thereof.

17. The method of claim 1, wherein the amine-containing macromolecule is selected from the group consisting of peptides, polypeptides, and proteins.

18. The method of claim 1, wherein the amine-containing macromolecule is selected from the group consisting of immunoglobulins, antibodies, and human serum albumin.

19. The method of claim 1, wherein the amine-containing macromolecule comprises a poly(lysine) salt.

20. The method of claim 19, wherein the poly(lysine) salt comprises poly(lysine hydrobromide).

21. The method of claim 1, wherein the yield of the substituted macromolecule is greater than 90%.

22. The method of claim 1, wherein the at least one carboxylate-containing molecule comprises DTPA, the at least one acid acceptor comprises triethylamine, the aprotic solvent comprises acetonitrile, the at least one carboxylate activating agent comprises isobutylchloroformate, and the amine-containing macromolecule comprises poly(lysine) salt.

23. The method of claim 1, wherein residence time of the activated carboxylate-containing molecule in the second solution is less than 10 minutes during addition to the first solution.

24. The method of claim 23, wherein the residence time of the activated carboxylate-containing molecule in the second solution is less than about 5 minutes during addition to the first solution.

25. The method of claim 1, further comprising isolating the substituted macromolecule.

26. The method of claim 1, wherein the amine-containing macromolecules comprises multiple amine-bearing repeat units, each amine-bearing repeat unit having at least one free amine group.

27. The method of claim 26, wherein the amine-containing macromolecule comprises multiple repeat units and at least 96 percent of the amine-bearing repeat units are conjugated with the carboxylate containing molecule.

28. The method of claim 26, wherein at least two equivalents of the carboxylate-containing molecule are used per one equivalent of the amine-bearing repeat unit.

29. The method of claim 26, wherein at least four equivalents of the carboxylate containing molecule are used per one equivalent of the amine-bearing repeat unit.

30. The method of claim 25, wherein the isolating step is performed using dialysis, ultrafiltration, tangential flow filtration, or a combination thereof.

31. The method of claim 26, wherein the amine-containing macromolecule comprises multiple repeat units and at least 95 percent of the amine-bearing repeat units are conjugated with the carboxylate containing molecule.

32. The method of claim 1, further comprising chelating the substituted macromolecule by a paramagnetic or superparamagnetic chemical to generate a labeled-carboxylate-containing substituted macromolecule.

33. A method of enhancing a magnetic resonance image of a subject comprising administering the labeled-carboxylate-containing substituted macromolecule produced by the method of claim 32 in a pharmaceutically acceptable carrier to the subject.

34. The method of claim 33, wherein the subject is a human.

35. The method of claim 32, wherein the substituted macromolecule comprises Gadolinium-DTPA substituted Polylysine.

36. The method of claim 1, wherein the yield of the substituted macromolecule is at least about 67%.

* * * * *